(12) United States Patent
Edwards

(10) Patent No.: US 11,071,841 B2
(45) Date of Patent: Jul. 27, 2021

(54) WEARABLE OXYGEN GENERATOR AND DOCKING STATION ENABLING HIGHER OXYGEN FLOW CAPACITY

(71) Applicant: Caire Inc., Ball Ground, GA (US)

(72) Inventor: Paul Edwards, Ball Ground, GA (US)

(73) Assignee: Caire Inc., Ball Ground, GA (US)

( * ) Notice: Subject to any disclaimer, the term of this patent is extended or adjusted under 35 U.S.C. 154(b) by 139 days.

(21) Appl. No.: 15/738,973

(22) PCT Filed: Jun. 22, 2016

(86) PCT No.: PCT/US2016/038712
§ 371 (c)(1),
(2) Date: Dec. 21, 2017

(87) PCT Pub. No.: WO2016/209925
PCT Pub. Date: Dec. 29, 2016

(65) Prior Publication Data
US 2018/0185602 A1    Jul. 5, 2018

Related U.S. Application Data

(60) Provisional application No. 62/182,845, filed on Jun. 22, 2015.

(51) Int. Cl.
*A61M 16/10* (2006.01)
*B01D 53/04* (2006.01)
(Continued)

(52) U.S. Cl.
CPC ........ *A61M 16/101* (2014.02); *A61M 16/021* (2017.08); *B01D 53/047* (2013.01);
(Continued)

(58) Field of Classification Search
CPC ............ A61M 16/101; A61M 16/0063; A61M 2209/086; B01D 53/04–053; B01D 2259/4533; B01D 2259/4541
See application file for complete search history.

(56) References Cited

U.S. PATENT DOCUMENTS

| | | | |
|---|---|---|---|
| 6,691,702 B2 | 2/2004 | Appel et al. | |
| 2002/0121191 A1* | 9/2002 | Warren | ................ B01D 53/047 95/11 |
| 2005/0160905 A1 | 7/2005 | Whitley et al. | |
| 2005/0161043 A1* | 7/2005 | Whitley | ............. B01D 53/0473 128/205.18 |
| 2005/0257686 A1* | 11/2005 | Occhialini | ........... B01D 53/047 95/96 |

(Continued)

FOREIGN PATENT DOCUMENTS

| | | |
|---|---|---|
| JP | 2004-560 A | 1/2004 |
| JP | 2011-143256 A | 7/2011 |
| WO | 2011044091 A2 | 4/2011 |

OTHER PUBLICATIONS

Extended European Search Report by the European Patent Office for Application No. PCT/US2016038712, dated Dec. 19, 2018.
Office Action in corresponding Chinese Application No. 201680043233.7, dated Oct. 31, 2019.
(Continued)

*Primary Examiner* — Valerie L Woodward
(74) *Attorney, Agent, or Firm* — Leason Ellis LLP

(57) ABSTRACT

A wearable oxygen concentrator can be used in both an ambulatory mode and a stationary mode. The wearable oxygen concentrator is physically connected to a docking station in the stationary mode such that it can draw power from the docking station and remain energy efficient in both modes. The disclosed oxygen generation system incorporates effective gas flow by means compressor configurations for use in lower flow ambulatory modes and higher flow stationary modes.

8 Claims, 7 Drawing Sheets

(51) Int. Cl.
*B01D 53/047* (2006.01)
*A61M 16/00* (2006.01)

(52) U.S. Cl.
CPC ..... *B01D 53/0446* (2013.01); *B01D 53/0473* (2013.01); *B01D 53/0476* (2013.01); *A61M 16/0063* (2014.02); *A61M 2202/0208* (2013.01); *A61M 2205/8206* (2013.01); *A61M 2209/086* (2013.01); *B01D 2253/104* (2013.01); *B01D 2253/108* (2013.01); *B01D 2256/12* (2013.01); *B01D 2257/102* (2013.01); *B01D 2257/80* (2013.01); *B01D 2259/4148* (2013.01); *B01D 2259/4533* (2013.01); *B01D 2259/4541* (2013.01)

(56) References Cited

U.S. PATENT DOCUMENTS

2006/0117957 A1* 6/2006 McCombs ............ A61M 16/10
  96/121
2006/0174877 A1* 8/2006 Jagger .................. A61M 16/10
  128/201.21

OTHER PUBLICATIONS

Second Office Action in corresponding Chinese Application No. 201680043233.7, dated Jun. 19, 2020.
Office Action in corresponding Japanese Application No. 2017-566344, dated Jul. 7, 2020.
Office Action in corresponding Japanese Application No. 2017-566344, dated Mar. 9, 2021.

* cited by examiner

WEARABLE OXYGEN GENERATOR AND DOCKING STATION ENABLING HIGHER OXYGEN FLOW CAPACITY

CROSS-REFERENCE TO RELATED APPLICATIONS

This application is a national stage application, filed under 35 U.S.C. § 371, of International Patent Application No. PCT/US2016/038712, filed on Jun. 22, 2016, which claims priority to U.S. Provisional Patent Application No. 62/182,845, filed Jun. 22, 2015. Priority to the aforementioned filing date is claimed and the entire contents of each are hereby incorporated herein by reference in their entireties and for all purposes.

BACKGROUND

The present disclosure relates to wearable and portable oxygen systems such as wearable pressure/vacuum swing adsorption oxygen systems adapted for use to provide breathable oxygen to patients. The disclosed devices and methods are suitable for use, for example, in ambulatory/wearable, mobile/portable and stationary applications.

Patients with Chronic Obstructive Pulmonary Disease (COPD) are often treated by oxygen augmentation wherein the patient is provided with air enriched in oxygen content. The treatment of a stationary or non-ambulatory patient typically involves the patient breathing from a pressure-swing absorber system that preferentially passes oxygen relative to nitrogen to the patient. These systems are electrically powered devices that in their most common form are cost-driven, energy inefficient, and heavy.

For mobile (i.e., ambulatory) patients, portable or wearable concentrators have been developed, driven by batteries and often using more energy efficient vacuum-pressure-swing cycles and pulsed-flow delivery to minimize power draw for extending battery life. However, batteries are heavy, and portable concentrators are typically usable for only a few hours without recharging or connecting to a main power source such as an AC source. For most patients, this means at least two devices are required for proper oxygen augmentation: one for use in in stationary conditions and another for use in mobile conditions. This can be expensive and cumbersome such that many patients must do without the convenience of a portable device.

SUMMARY

Disclosed is a wearable oxygen concentrator that can be used in both an ambulatory mode and a stationary mode and remain energy efficient in both modes. The disclosed oxygen generation system incorporates effective gas flow by means of improved and novel compressor configurations for use in lower flow ambulatory modes, all the way up to higher flow stationary applications, as described in detail below.

A wearable compact oxygen concentrator unit that is compact and efficient is desirable for a patient. For example, the applicant has determined that a wearable compact oxygen concentrator having the following non-limiting specifications is desirable for ambulatory patients and the disclosed system conforms to such specifications: it produces and delivers oxygen at 2.0 liters per minute (lpm) of continuous purified oxygen flow, weighs less than 9 pounds (or less than 7 pounds), and last about 2 hours on a single battery charge. These specifications, which are non-limiting examples, are challenging and require a two-fold reduction in weight compared with the most advanced oxygen concentrators now in production.

The disclosed wearable device can be carried by an ambulatory patient as the patient goes about with his or her daily life. This device can be carried, for example, by a medic, incorporated into evacuation platforms, carried by a patient, carried by a soldier, or a person at high altitude/low oxygen environments. Such a device is well suited for ambulatory patients and would require adaptation for stationary use. Patients are prescribed oxygen at rates greater than 2 liters per minute (lpm), primarily when they are stationary or asleep. The flow requirements for stationary use (when attached to a docking station) can be up to, for example, 5 lpm. Such a device/system draws wall mounted AC power instead of battery power when in use. This disclosure relates to configurations by which a 2 lpm wearable device is mechanically coupled in combination with additional equipment such as a docking station so that the wearable device can be converted to a 5 lpm stationary unit.

The disclosed devices and methods enable the use of the wearable oxygen concentrator for higher flow stationary use when required and when main power is available. This allows the use of just one device, a wearable oxygen concentrator, for a whole range of patient oxygen flow demand.

Oxygen concentrators are devices that extract oxygen from the air. These devices avoid the hazards of storing oxygen under pressure. They can supply oxygen continuously, for as long as energy is available from batteries, generators or other power sources. Oxygen is often needed by patients in outside or extreme conditions, such as to keep a wounded soldier alive and provide for other patients with COPD and/or emphysema. It may be needed in remote areas, with no electricity and no supplies beyond what a person can carry. It may also be needed for patients in their everyday lives and for longer durations in small spaces such as air travel.

A desirable oxygen source is a light, efficient, wearable device that works with in-built rechargeable battery, and can supply oxygen continuously for couple of hours at a time. No current technology truly meets these requirements due to technical hurdles.

The disclosed devices include an ambulatory or portable (i.e., wearable) oxygen concentrator that combines with a booster base powered by a source of electricity, such as mains-supplied (household) electricity. The portable concentrator may include a rotary structured adsorbent system to enable rapid VPSA cycling in a small-volume array of adsorbent beds, providing lightweight and efficient concentration from battery power at lower flow rates for portable use. The booster base may include auxiliary equipment that enables greater air flow (i.e., more compressor and/or vacuum pump capacity), used in combination with faster rapid cycle pressure swing adsorption (PSA) or Vacuum-Pressure Swing Adsorption (VPSA) cycling in the adsorbent beds; together to provide the higher flows typical of stationary concentrators. The booster base may also include other suitable auxiliaries like humidification and sound dampening as appropriate for in-home use.

Details of one or more implementations are set forth in the accompanying drawings and in the description below. Further features, aspects, and advantages will become apparent from the description, the drawings, and the claims.

DETAILED DESCRIPTION

Before the present subject matter is further described, it is to be understood that this subject matter described herein is not limited to particular embodiments described, as such may of course vary. It is also to be understood that the terminology used herein is for the purpose of describing a particular embodiment or embodiments only, and is not intended to be limiting. Unless defined otherwise, all technical terms used herein have the same meaning as commonly understood by one skilled in the art to which this subject matter belongs.

Disclosed are systems and methods for providing oxygen augmentation to a patient in the form of a wearable oxygen concentrator that can transition to a stationary mode when physically connected to a docking station. The device may be ordinarily used in an ambulatory mode and may deliver higher oxygen flows to patient in a stationary (or non-ambulatory) mode. The disclosed systems and methods provide a versatile oxygen generation system incorporating effective gas flow by means of improved and novel compressor flow configurations for use in lower flow ambulatory all the way up to higher flow stationary applications.

In a non-limiting embodiment, a portable and wearable concentrator produces and delivers oxygen at up to 2.0 lpm of continuous purified oxygen flow, weighs less than 9 pounds (or less than 7 pounds), and last for about 2 hours on a single battery charge. The wearable concentrator includes a rotary adsorbent module containing structured adsorbent beds and rotary valve, a compressor having compressor section and vacuum section, a rechargeable battery, piping (i.e. flow lines), electrical, fans, motors, frames, cover and instrumentation and controls. This allows a patient to carry the device easily and in comfort.

Figure 1:
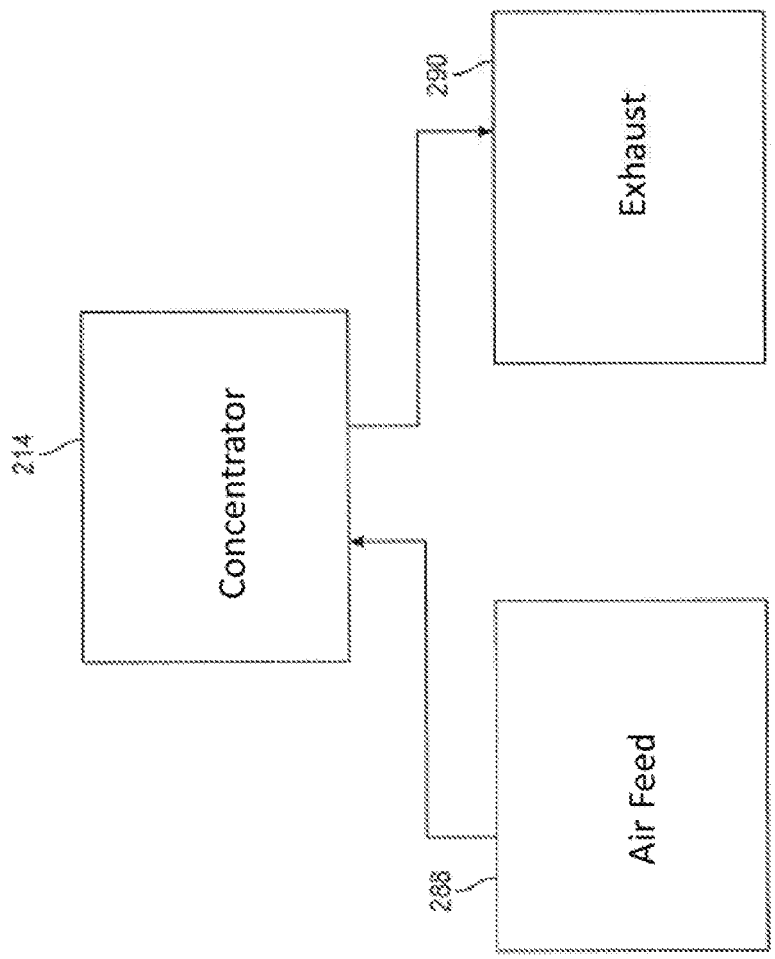
FIG. 1 shows a schematic view of a first embodiment of a wearable oxygen concentrator.

A simplified flow schematic of a wearable concentrator system is shown in FIG. 1. The wearable oxygen concentrator system includes the concentrator 214, which is fluidly connected to an air feed 288 and an exhaust 290. Air enters or feeds into the system via the air feed 288 and exits or exhausts from the system via the exhaust 290. The concentrator includes an outer housing and one or more user-actuatable control elements, such as physical buttons, switches, etc. and/or a touch screen.

In an embodiment the system includes a docking station (schematically represented in FIG. 3) that can be physically docked to the wearable oxygen concentrator 214 to enable the wearable concentrator to thereby achieve a stationary mode that provides higher oxygen flow relative to the wearable or ambulatory mode. When docked, the docking station and wearable system are electrically connected to permit electrical power to be transferred between the two devices. The systems are also fluidly connected to permit fluid transfer between the devices. In the stationary mode, the docking station device draws power from a power source such as a wall outlet or electrical grid and transfers that power to the wearable concentrator system. In an example embodiment, higher oxygen flows can be as high as 10 lpm and in another embodiment up to 5 lpm on stationary mode. The docking station may include an air input conduit (air feed), an exhaust conduit, a compressor, a vacuum pump, a wall/grid connection, heat sink/exchanger, sound abatement, piping and instrumentation and controls.

The compressor used in the wearable oxygen concentrator is compact, efficient and light-weight, and has distinct compression and vacuum sections. The adsorbent section can include structured adsorbent beds for lower pressure drop, faster kinetics, and better uniformity and heat management. The compressor may be of a swing type or a scroll type mechanical configuration. Alternately, the compressor could be linear type or reciprocating type configuration to enable significant flow ramp up.

Figure 2A:
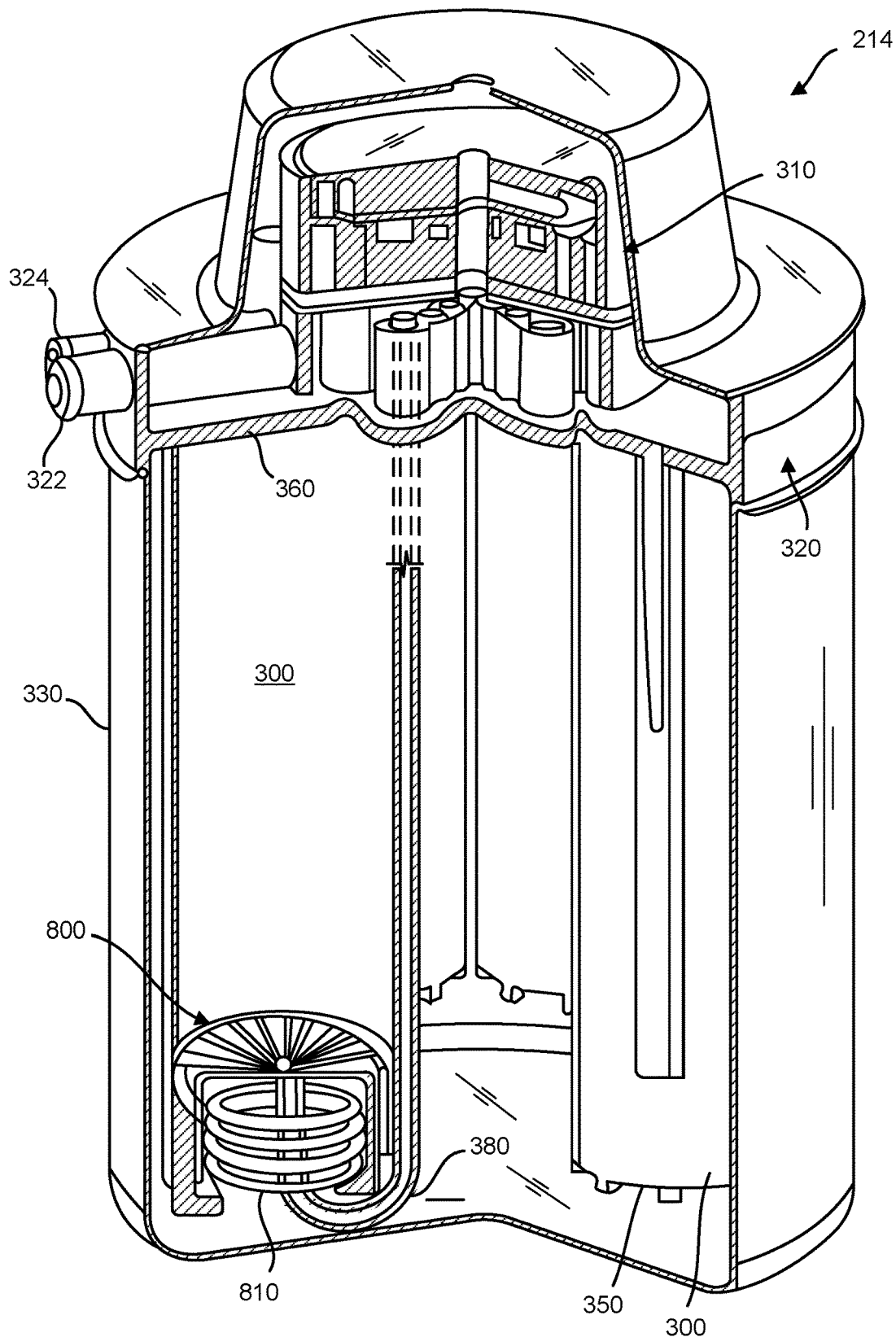
FIGS. 2A and 2B are a cutout and exploded views of an example concentrator.
Figure 2B:
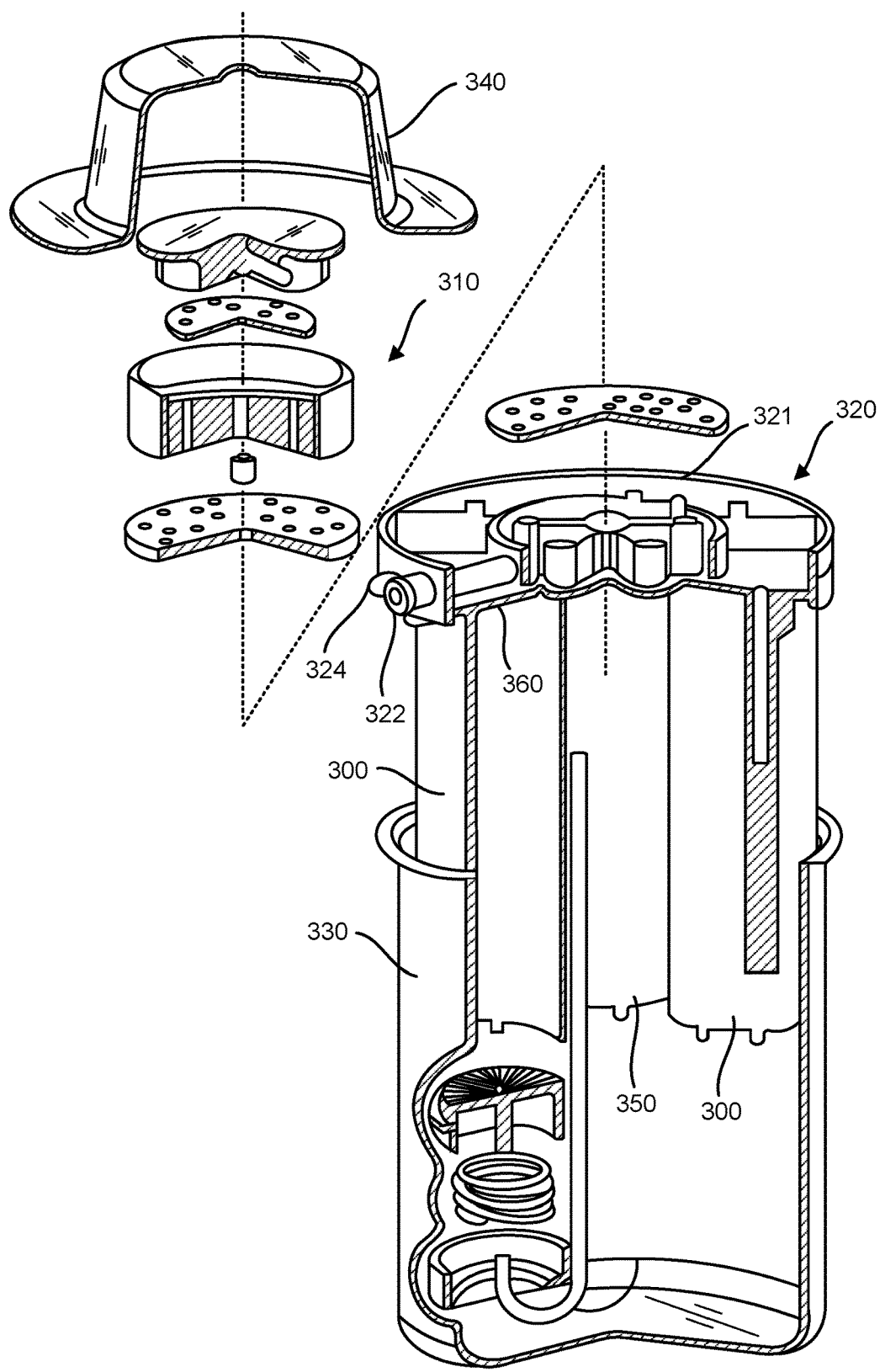

FIGS. 2A and 2B are a cutout and exploded view, respectively, of an example concentrator 214 that may be used as the oxygen generator shown in FIG. 1 and other embodiments. As shown, the concentrator 214 includes adsorption beds 300, each containing a bed of adsorbent material which is selective for a particular molecular species of fluid (liquid or gas) or contaminant, a rotary valve assembly 310 for selectively transferring fluids through the adsorption beds 300, an integrated tube-assembly and a manifold 320, a product tank cover 330, and a valve assembly enclosure 340. In some embodiments, the adsorption beds 300 are molded plastic vessels surrounded by the product tank cover 330, which may be made of metal (e.g., aluminum). In another embodiment, the concentrator is configured according to the oxygen concentrator and spin pump described in U.S. patent application Ser. No. 14/510,904 (which is incorporated herein by reference in its entirety) filed Oct. 9, 2014 and entitled "Spin Pump With Spun-Epicyclic Geometry."

Each adsorption bed 300 includes a product end 350 and a feed end 360. The product ends 350 of the beds 300 communicate with incoming product passages of the manifold 320 through product lines 380 for communication with the rotary valve assembly 310. The manifold 320 may also include outgoing product passages that communicate the rotary valve assembly 310 with the interior of the product tank 330, an incoming feed passage that communicates the rotary valve assembly 310 with a feed pressure line 322, and a vacuum chamber that communicates the rotary valve assembly 310 with a vacuum pressure line. A product delivery line 324 communicates with the interior of the product tank 330. A vacuum pressure line may communicate directly or indirectly with a vacuum generator for drawing exhaust gas from the concentrator.

In operation, air flows from the compressor to the feed pressure line 322, through the incoming feed passage of the manifold 320. From there, air flows to the rotary valve assembly 310 where it is distributed back through outgoing feed passages of the manifold 320. From there, the feed air flows to the feed ends 360 of the adsorption beds 300. The adsorption beds 300 include adsorbent media that is appropriate for the species that will be adsorbed. For oxygen concentration, a packed particulate adsorbent material that adsorbs nitrogen relative to oxygen in the feed air may be used so that oxygen is produced as the non-adsorbed product gas. An adsorbent such as a highly Lithium exchanged X-type Zeolite may be used. A layered adsorbent bed that contains two or more distinct adsorbent materials may also be used. As an example, for oxygen concentration, a layer of activated alumina or silica gel used for water adsorption may be placed near the feed end 360 of the adsorbent beds 300 with a lithium exchanged X-type zeolite used as the majority of the bed toward the product end 350 to adsorb nitrogen.

The resulting product oxygen gas flows towards the products ends 350 of the adsorption beds 300, through the product lines 380, through incoming product passages of the manifold 320, and to the rotary valve assembly 310, where it is distributed back through the manifold 320 via the outgoing product passage and into the product tank 330. From the product tank 330, oxygen gas is supplied to the user through the product delivery line 324 and/or the supply line 221.

The concentrator 214 separates oxygen gas from air for eventual delivery to a user 208. The concentrator 214 connects to the user via a supply line which may include one or more of, for example, a pressure sensor, a temperature sensor, a pump, a low-pressure reservoir, a supply valve, a flow and purity sensor, and a conservation device 290. These various components constituting the supply line 221 may be coupled using tubes, connectors, etc. The pump may be driven by a motor. The oxygen may be stored in the low-pressure reservoir and delivered to the user. The supply valve may be used to control the delivery of oxygen gas from the low-pressure reservoir to the user at atmospheric pressure.

In some implementations, the concentrator may also be configured to dispel exhaust gas. In some embodiments, a vacuum generator, which may also be driven by a motor and integrated with a compressor, draws exhaust gas from the concentrator to improve the recovery and productivity of the concentrator. The exhaust gas may exit the device through an exhaust muffler. A pressure transducer may be located between the concentrator and the vacuum generator to get a pressure reading of the exhaust flow from the concentrator.

In some embodiments, the concentrator 214 may be an Advanced Technology Fractionator (ATF) that may be used for medical and industrial applications. The ATF may implement a pressure swing adsorption (PSA) process, a vacuum pressure swing adsorption (VPSA) process, a rapid PSA process, a very rapid PSA process or some other process. If a PSA or VPSA process is implemented, the concentrator may include a rotating valve or a non-rotating valve mechanism to control air flow through multiple sieve beds. The sieve beds may be tapered so that they have larger diameter where gaseous flow enters the beds and a smaller diameter where gaseous flow exits the beds. Suitable sieve materials that may be used in the ATF concentrator 214 include LithiumX Zeolite that allows for a high exchange of Lithium ions. Other types of concentrators or air-separation devices, including membrane separation types and electrochemical cells (hot or cold), may also be used.

Figure 3:
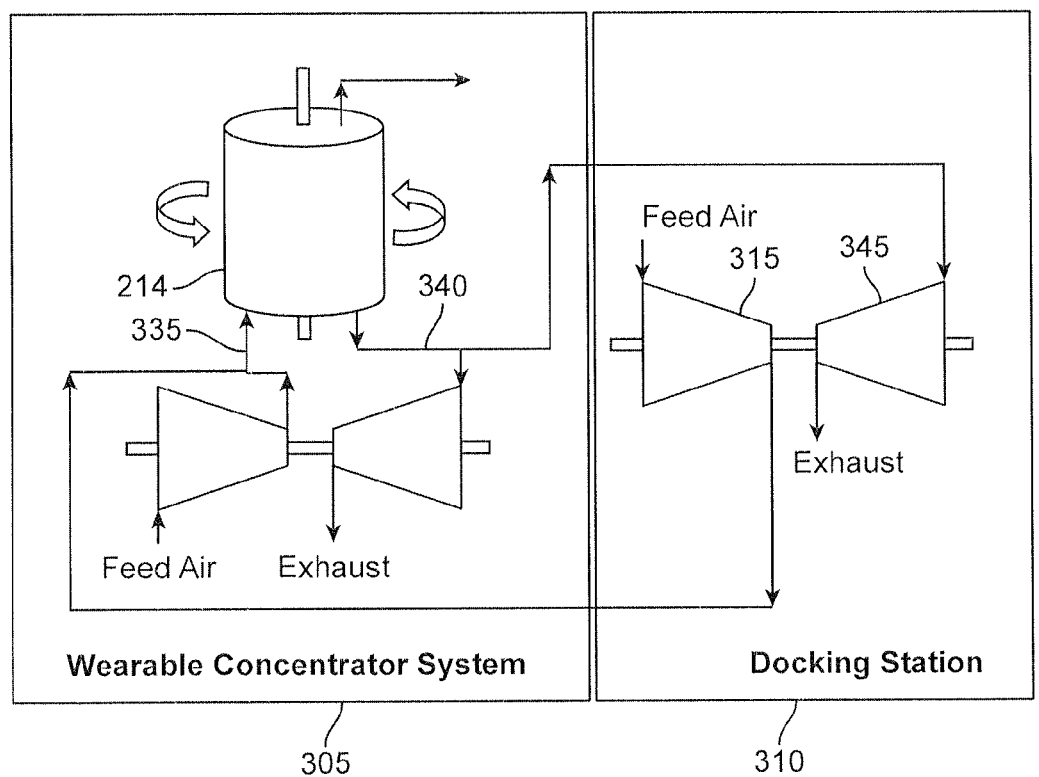
FIG. 3 shows a schematic view of the first embodiment connected to a docking station both on compression and vacuum flows.

In an embodiment shown in FIG. 3, the wearable concentrator system 305 is mechanically and fluidly connected to a docking station both on a compression flow line or conduit and on vacuum flow line or conduit. A compressor portion or side 335 of the wearable concentrator is physically connected to a compressor pump 315 of the docking station 310. A vacuum portion or side 340 of the wearable concentrator is connected to a vacuum pump 345 of the docking station. The compressor and vacuum pumps in the docking station can be integrated on a single, rotatable shaft, such as described in U.S. patent application Ser. No. 14/510,904 (which is incorporated herein by reference in its entirety) filed Oct. 9, 2014 and entitled SPIN PUMP WITH SPUN-EPICYCLIC GEOMETRY. The wearable concentrator rotary module containing structured adsorbent is sped up to a predetermined value, such as, for example, ~3× to deliver 5 lpm oxygen flow. The combined device draws power from a power source such as a wall outlet or electrical grid (mains power) and not from a rechargeable battery of the system when in stationary mode. The system is in stationary mode when the wearable oxygen concentrator system is attached to the docking station.

Figure 4:
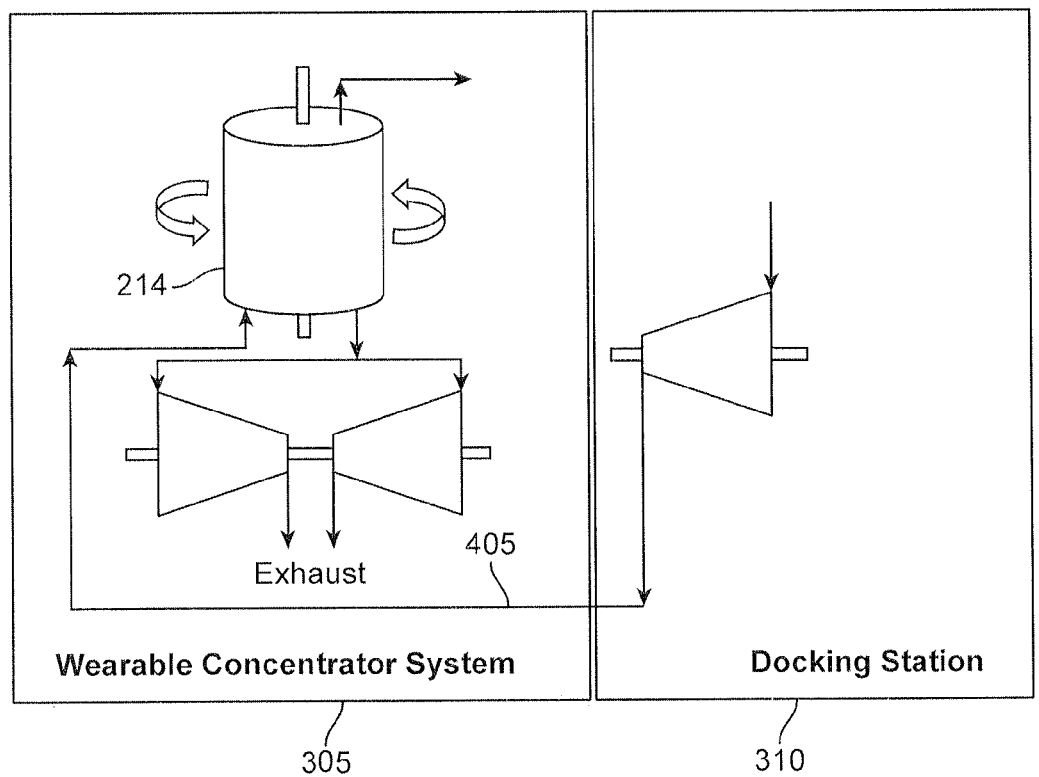
FIG. 4 shows a schematic view of a second embodiment connected to a docking station to compression compressor flow.

In another embodiment shown in FIG. 4, the wearable concentrator system 305 is fluidly connected to the docking station 310 on the compression flow only via an air feed conduit 405. The flows to and from the compressor section in the wearable concentrator are switched such that the compressor of the wearable concentrator becomes a vacuum pump of larger capacity. The compressor side of the wearable concentrator is connected to docking station compressor 410. The vacuum side of the wearable concentrator exhausts to ambient via an outlet conduit 415. The wearable concentrator rotary module containing structured adsorbent is sped up ~3× to deliver 5 lpm oxygen flow. The combined device will draw power from wall/grid and not from the rechargeable battery.

Figure 5:
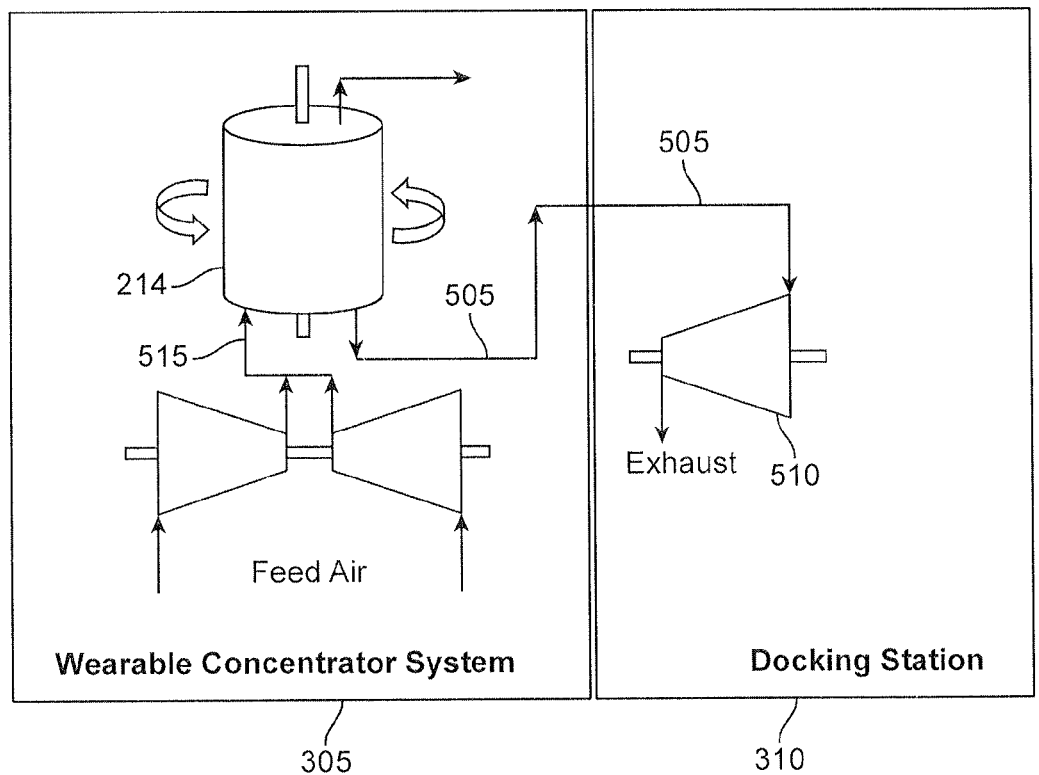
FIG. 5 shows a schematic view of a third embodiment connected to a docking station to compression vacuum flow.

In another embodiment shown in FIG. 5, the wearable concentrator system 305 fluidly connects to a docking station 310 on the vacuum flow only such that the vacuum flow exhausts toward an exhaust conduit that is coupled to a compressor of the docking station via a conduit 505. The flows to and from the vacuum section in the wearable concentrator are switched such that the compressor of the wearable concentrator becomes a compressor pump of larger capacity. The vacuum side of the wearable concentrator is connected to the docking station vacuum pump 510; the compressor side 515 of the wearable concentrator draws ambient air via an inlet conduit connected to the oxygen concentrator. The wearable concentrator rotary module containing structured adsorbent is sped up ~3× to deliver 5 lpm oxygen flow. The combined device will draw power form wall/grid and not from the rechargeable battery.

Figure 6:
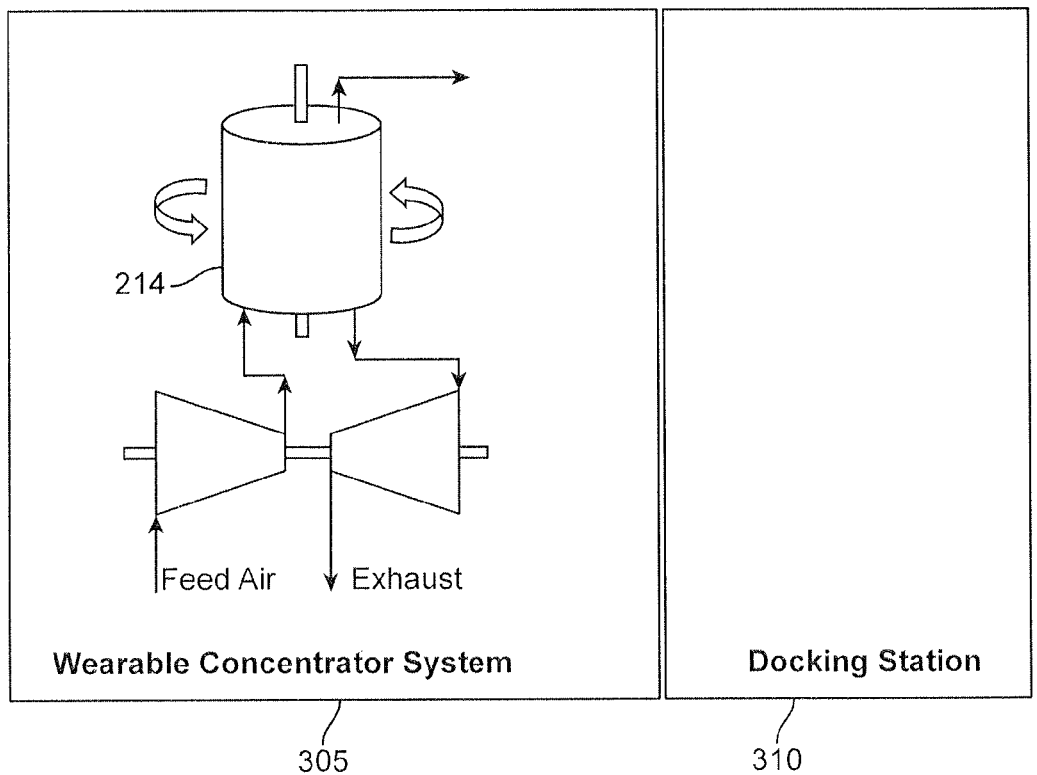
FIG. 6 shows a schematic view of a fourth embodiment not fluidly connected.

In another embodiment according to the present disclosure shown in FIG. 6, the wearable concentrator system 305 is not fluidly connected to the docking station on either compression or vacuum flows. The compressor and vacuum flows are ramped up by a factor of ~3×. The compressor used in the wearable concentrator device is capable of such significant ramp up of flows. The compressor can be a linear type or a reciprocating type to enable such ramp up of flows. The wearable concentrator rotary module containing structured adsorbent is sped up ~3× to deliver 5 lpm oxygen flow. The combined device will draw power from wall/grid and not from the rechargeable battery Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

The invention claimed is:

1. An oxygen concentration system, the system comprising:
   a patient portable unit having an oxygen concentrator configured to generate a constant level of gaseous oxygen flow and deliver the gaseous oxygen to a patient, the patient portable unit being portable by the patient and weighing less than nine pounds, wherein the patient portable unit is configured to deliver gaseous oxygen solely generated therein to a patient up to a first maximum flow rate, wherein the first maximum flow rate is greater than 1.5 lpm, when in a standalone mode and not attached to a docking station, the portable unit including a rechargeable battery;

a docking station without an oxygen concentrator that is configured to be at least electrically and fluidly connected to the patient portable unit, wherein the patient portable unit is configured to deliver continuous gaseous oxygen to a patient up to a second maximum flow rate greater than the first when in a stationary mode and attached to the docking station, wherein the second maximum flow rate is at least two times greater than the first maximum flow rate and the second maximum flow rate is generated without the use of an additional oxygen concentrator, and wherein the patient portable unit draws power from the docking station to operate its oxygen concentrator when the patient portable unit is attached to the docking station, which drawn power is greater than the power drawn from the rechargeable battery.

2. The system of claim 1, wherein the oxygen concentrator is fluidly connected to an air feed and an exhaust.

3. The system of claim 1, wherein a compressor portion of the oxygen concentrator is physically connected to a compressor pump of the docking station, and a vacuum portion of the oxygen concentrator is connected to a vacuum pump of the docking station when in the stationary mode.

4. The system of claim 3, wherein the compressor pump and the vacuum pump of the docking station are integrated on a single, rotatable shaft.

5. The system of claim 1, wherein a compressor portion of the oxygen concentrator is physically connected to a compressor pump of the docking station, and a vacuum portion of the oxygen concentrator is also connected to the compressor pump of the docking station when in the stationary mode.

6. The system of claim 5, wherein the compressor pump and a vacuum pump of the docking station are integrated on a single, rotatable shaft.

7. The system of claim 5, wherein the vacuum portion of the oxygen concentrator exhausts to ambient air via an outlet conduit connected to the compressor pump.

8. The system of claim 7, wherein the compressor side of the oxygen concentrator draws ambient air via an input conduit.

* * * * *